United States Patent
Brown et al.

(10) Patent No.: US 6,706,768 B2
(45) Date of Patent: Mar. 16, 2004

(54) PRODUCTION AND USE OF NOVEL ALKOXYLATED MONOESTERS

(75) Inventors: James H. Brown, Scottsdale, AZ (US); Robert Kleiman, Mesa, AZ (US); John C. Hill, Mesa, AZ (US)

(73) Assignee: International Flora Technologies, Ltd., Gilbert, AZ (US)

( * ) Notice: Subject to any disclaimer, the term of this patent is extended or adjusted under 35 U.S.C. 154(b) by 136 days.

(21) Appl. No.: 10/104,723

(22) Filed: Mar. 21, 2002

(65) Prior Publication Data

US 2003/0181600 A1 Sep. 25, 2003

(51) Int. Cl.[7] .............................. B01F 17/34; A61K 7/06
(52) U.S. Cl. ........................ 516/74; 516/204; 554/149; 424/59; 424/70.31; 424/74; 514/785; 514/787
(58) Field of Search ................... 516/74, 204; 508/450; 514/785, 767; 424/59, 70.31, 74; 554/30, 125, 149

(56) References Cited

U.S. PATENT DOCUMENTS

| | | | | |
|---|---|---|---|---|
| 2,612,509 A | * | 9/1952 | Griffin | 554/227 |
| 4,246,285 A | * | 1/1981 | Van Duzee | 514/785 |
| 4,329,298 A | * | 5/1982 | Brown et al. | 554/125 |
| 4,664,914 A | * | 5/1987 | Stillman | 424/401 |
| 4,749,517 A | * | 6/1988 | Chwang et al. | 508/501 |
| 5,405,980 A | * | 4/1995 | Baumann | 554/162 |
| 5,621,148 A | * | 4/1997 | Baumann | 568/619 |
| 5,776,441 A | * | 7/1998 | Scancarella et al. | 424/61 |
| 5,814,310 A | * | 9/1998 | Nagy et al. | 424/65 |
| 6,299,891 B1 | * | 10/2001 | Leverett | 424/59 |
| 6,582,748 B1 | * | 6/2003 | Loh et al. | 426/601 |

FOREIGN PATENT DOCUMENTS

| | | | |
|---|---|---|---|
| WO | WO 9937274 | * | 7/1999 |
| WO | WO 0103664 A1 | * | 1/2001 |

* cited by examiner

Primary Examiner—Daniel S. Metzmaier
(74) Attorney, Agent, or Firm—The Halvorson Law Firm

(57) ABSTRACT

Described is an alkoxylated composition that comprises a family of trans carbon-carbon double bond free compositions that generally have melting points that range from 30–80° C., preferably with melting points between 55–58° C. and with a solubility profile compatible with a broad range of cosmetic and industrial chemical bases. At room temperature (~20° C.), this family of compositions varies from pourable liquids, to soft creams, to pasty waxes, to a brittle hard material. These compounds, whether used pure or when combined with other carrier and vehicle components (including other additives, thickeners or binders) can form excellent carrier and vehicles for delivery of compositions for use in the cosmetic, personal care and/or pharmaceutical field, including the cosmeceutical field where cosmetic compositions also provide pharmaceutical or other therapeutic benefits.

7 Claims, 1 Drawing Sheet

US 6,706,768 B2

PRODUCTION AND USE OF NOVEL ALKOXYLATED MONOESTERS

FIELD OF THE INVENTION

The present invention relates to novel alkoxylated monoesters, their uses, and methods of manufacture thereof. More specifically, the present invention is related to ethoxylated monoesters, propoxylated monoesters and ethoxylated/propoxylated monoesters produced from partially or wholly trans-free double-bonded jojoba ester products.

BACKGROUND

Natural products and their derivatives are increasingly favored in the cosmetics industry since consumers have become more environmentally sensitive. Further, consumers have recognized the value of many unique properties displayed by natural products and their derivatives.

One common method of producing natural products for the cosmetic industry is to extract an oil or wax from the seed of a plant. Oils and waxes are a group of organic substances that form an important and useful part of the cosmetic and other industries. Generally, waxes are solid and oils are liquid at ordinary room temperatures. However, some tropical products, which are liquids in their sites of origin, become solids in cooler climates, often retain the name originally given, e.g., palm oil and coconut oil. Waxes and oils are derived from both plant and animal sources.

Chemically most fats and oils are either simple or mixed glyceryl esters of organic acids belonging to the fatty-acid series (triglycerides). Triglycerides are esters formed from glycerol and three fatty acids that may be identical or different from each other. In a simple triglyceride such as tripalmitin or tristearin, all three fatty-acid groups are identical. In a mixed triglyceride, two or even three different fatty-acid groups are present. Most oils and waxes contain mixed triglycerides.

Waxes are often found as trace components of triglyceride oils or can be extracted in a more pure form from certain botanical and animal sources. Sunflower and corn oils contain natural waxes, while jojoba, carnauba and candelillia are examples of waxes found naturally in a more pure form. Beeswax and lanolin are examples of natural waxes of insect and animal origin. These example waxes range from the liquid, unsaturated jojoba oil to the almost completely saturated sunflower wax.

In order to control, or modify, various properties, such as solubility or melting point, of oils and waxes, certain modifications can be introduced into the triglyceride and/or wax ester structure. One such modification is the introduction of ethylene oxide (ETO) and/or propylene oxide (PO) units to the hydroxyl function of a hydrolyzed triglyceride or wax ester. It has been found that by controlling the number of units ETO or PO added, various properties such as solubility and melting point can be adjusted in the oil or wax. Generally, it has been found that compounds become more water soluble as the level of ethoxylation increases, but become more alcohol soluble, more oil soluble and more fluid as the level of propoxylation increases. Compounds that are ethoxylated, as well as propoxylated, acquire both water and alcohol solubility. Because ethoxylation also raises the melting point of materials, ethoxylates vary in form, depending on the level of ethoxylation. For instance, when a liquid starting material is ethoxylated with approximately 15 moles of ethylene oxide, it may become solid or semi solid at room temperature. Propoxylates, however, are more often liquids because they contain branched polyoxypropylene chains. Branching tends to keep materials fluid.

Another method of altering the melting points of oils and waxes is to add hydrogen to points of unsaturation within the oil or wax molecule. The addition of hydrogen is typically accomplished under several atmospheres of pressure at elevated temperatures and in the presence of metal catalysts, such as nickel or palladium. This hydrogenation process can be continued until all points of unsaturation within the oil or wax molecule are saturated with hydrogen, or the reaction can be stopped at some point short of achieving a fully saturated oil or wax. The melting point of the oil or wax generally increases as a linear function of the amount of hydrogen that has been added. A hydrogenation reaction is said to yield "partially hydrogenated" material when stopped short of achieving a "fully saturated" oil or wax. The melting point of these "partially hydrogenated" materials is less than the melting point of the "fully saturated" material and higher than the melting point of the starting oil or wax.

Although partial hydrogenation is a means of adjusting the melting point of an oil or wax, this partial hydrogenation process results in the formation of unwanted "trans" isomers. These trans isomers have been shown to be harmful in human nutrition and have an inhibitory effect on the natural metabolic pathway whereby prostaglandins are created in the skin.

While alkoxylation is a process whereby the melting points and solubility of various oils and waxes can be modified, there is a need to expand the range of melting points of alkoxylated materials. Partial hydrogenation to achieve a higher melting point is not desirable because of the formation of unwanted trans isomers. There is a need to have a broad range of melting points of alkoxylated oils and waxes with elevated melting points that are free or substantially free of trans isomers created through partial hydrogenation.

SUMMARY OF INVENTION

It is an object of the present invention to provide a composition that is useful for cosmetic and other applications.

It is another object of the present invention to provide a substantially trans carbon-carbon double bond free composition comprising an alkoxylated wax ester, where the wax ester is substantially trans carbon-carbon double bond free prior to being alkoxylated.

It is yet another object of the present invention to provide the composition above wherein the alkoxylate is prepared using ethylene oxide.

It is still yet another object of the present invention to provide the composition above wherein the alkoxylate is prepared using propylene oxide.

It is a further object of the present invention to provide the composition above wherein the alkoxylate is prepared using a mixture of ethylene oxide and propylene oxide.

It is yet a further object of the present invention to provide the composition above where the alkoxylation is roughly 150 mol equivalents.

It is still yet a further object of the present invention to provide a substantially trans carbon-carbon double bond free composition comprising an alkoxylated wax ester, where the wax ester is substantially trans carbon-carbon double bond free prior to being alkoxylated and where the wax ester is a partially saturated wax ester, the wax ester being substantially trans carbon-carbon double bond free prior to partial saturation.

It is another object of the present invention to provide the composition above wherein the alkoxylate of the trans free wax ester is prepared using ethylene oxide.

It is still another object of the present invention to provide the composition above wherein the alkoxylate is prepared using propylene oxide.

It is yet another object of the present invention to provide the composition above wherein the alkoxylate is prepared using a mixture of ethylene oxide and propylene oxide.

It is still yet another object of the present invention to provide the composition above where the alkoxylation is roughly 150 mol equivalents.

It is a further object of the present invention to provide a substantially trans carbon-carbon double bond free composition comprising an alkoxylated wax ester, where the wax ester is substantially trans carbon-carbon double bond free prior to being alkoxylated where the wax ester that is substantially trans carbon-carbon double bond free prior to being alkoxylated is a fully saturated wax ester, the saturated wax ester being substantially trans carbon-carbon double bond free prior to partial saturation.

It is yet a further object of the present invention to provide the composition above wherein the alkoxylate is prepared using ethylene oxide.

It is still a further object of the present invention to provide the composition above wherein the alkoxylate is prepared using propylene oxide.

It is still yet a further object of the present invention to provide the composition above wherein the alkoxylate is prepared using a mixture of ethylene oxide and propylene oxide.

It another object of the present invention to provide the composition above where the alkoxylation is roughly 150 mol equivalents.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

Figure 1:
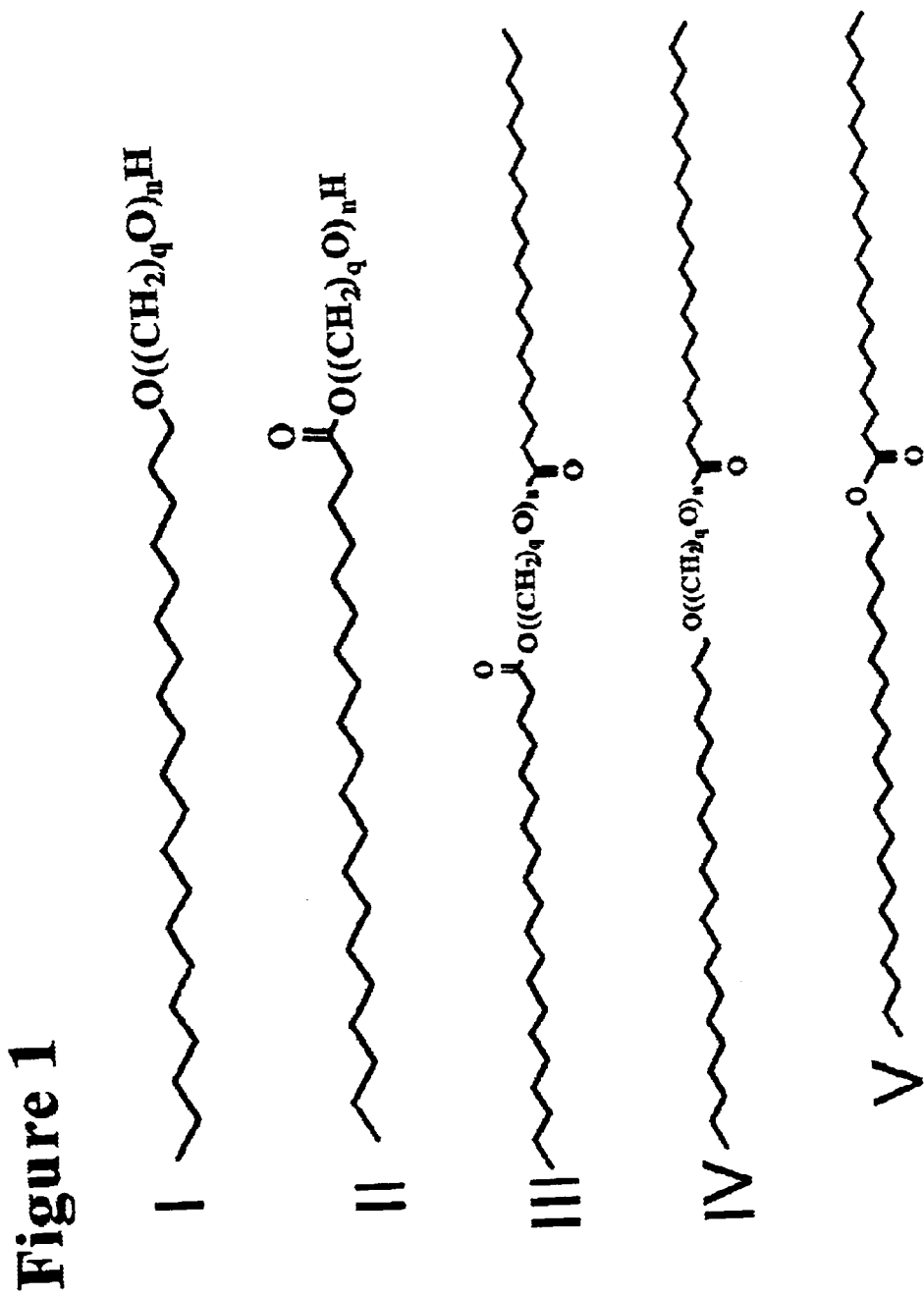
FIG. 1 illustrates an example reaction process for the polyalkoxylation of a hydroxy-free fatty compound. The products illustrated show only majority products, it being recognized that many additional minority components may be produced (but in small concentrations).

The present invention is a novel composition that is useful as an ingredient in pharmaceuticals, neutraceuticals, and cosmeceuticals. Preferably, the compositions according to the present invention are used in shampoos, hair conditioners, skin conditioners, deodorant sticks, lipsticks, toners, skin cleansers, and the like. Additionally, the compositions according to the present invention may be used as "water soluble" adhesives since their water solubility is greater than traditional, oil based, adhesives, and have sufficient stickiness and tackiness to hold items while in the solid state.

Preferably, the composition of the present invention comprises a family of trans carbon-carbon double bond free compositions that generally have melting points that range from 30–80° C., preferably with melting points between 55–58° C. At room temperature (~20° C.), this family of compositions varies from pourable liquids, to soft creams, to pasty waxes, to a brittle hard material. However, the preferred embodiment is solid below 55° C. The composition of the present invention may be blended with different melting point components within the family to form other products with selected melting points and specific physical properties or feel. These compounds, whether used pure or when combined with other carrier and vehicle components (including other additives or binders) can form excellent carrier and vehicles for delivery of compositions for use in the cosmetic, personal care and/or pharmaceutical field, including the cosmeceutical field where cosmetic compositions also provide pharmaceutical or other therapeutic benefits. Typical materials with which the compound according to the present invention may be blended in accordance with the practice of the present invention include, but are not limited to, cosmetic oils and waxes, both natural and synthetic, including hydrogenated or partially hydrogenated oils, silicon oils, mineral oils, long chain esters, vitamins (especially vitamin E), long chain fatty acids, alcohols, cosmeceuticals, pigments, botanical extracts, esters and ethers, dimers, trimers, oligomers, and polymers, and the like. These blended compositions may of course be combined with the active ingredients intended to be delivered by the composition used in the present invention.

The compositions according to the present invention may be blended with other waxes, oils, thickeners, abrasive materials, pigments, and the like to prepare a "water soluble" adhesive wax. This "water soluble" adhesive wax finds use in industries where temporary adhesives are needed, especially industries where the adhesives are needed to be soluble enough in water to wash residual adhesive off of attached surfaces.

Preferably, the present invention has a partially saturated component. Typical alcohol-free fatty compounds are single ester waxes and oils such as jojoba oil, rice bran wax, sunflower wax, candellia wax, beeswax, corn oil wax, and the like. In their natural state (obtained directly from the source seed or nut), the liquid waxes and oils typically contain one or more double bonds (points of unsaturation). The partially saturated component of the instant invention is unique in that it has a single carbon-carbon double bond that is a cis isomer. This configuration is necessarily present or implicit in some of the processes of manufacture as disclosed herein. Complete hydrogenation of unsaturated compounds, of course, leads to a trans free resultant. This is because all double bonds, whether cis or trans, are hydrogenated and thus removed. However alternate embodiments of the present invention utilize partially saturated compounds. Partial saturation accomplished via partial hydrogenation (an incomplete hydrogenation reaction) yields a quantity of the trans isomer of the carbon-carbon double bond. This is true even if the carbon-carbon double bond is originally in the cis isomer. However, when the partial saturation is accomplished through interesterification, as in the present invention, all carbon-carbon double bonds originally in the cis isomer remain in the cis isomer. Thus, since the starting unsaturated compounds used herein contain no trans carbon-carbon double bonds, but cis carbon-carbon double bonds, any partially saturated resultant prepared through interesterification will be essentially trans free.

The present invention allows for the production of fatty compositions with predetermined physical properties, such as melting point and solubility profile. This is important in the cosmetics and other industries where various formulations require components that melt either above or below normal skin or room temperatures or which are soluble in, or compatible with, a wide variety of cosmetic bases. Preferably, the desired melting characteristics of the present invention is accomplished by first adjusting the physical properties of the unsaturated fatty starting materials. This is accomplished by controlling the partial saturation of the unsaturated fatty compound through transesterification. Then, when the partially saturated fatty compound has the desired physical properties (which are not necessarily the same as the physical properties of the final product), the physical properties of the product of this invention may be tuned by varying the degree and composition (ratios) of the alkoxylate reactants. The result is an array of alkoxylated wax esters whose physical properties, such as melting points and solubility, are varied. Thus, the present invention is a composition that results from the polyalkoxylation of a fatty compound. Preferably, this fatty compound is trans-free and alcohol free.

In one embodiment, the present invention is a composition that results from the addition of $(CH_2CH_2O)_x$ or $(CH_2CH_2CH_2O)_y$ to a fully hydrogenated (saturated) alcohol-free fatty compound. This addition, in the absence of an alcohol ligand, is accomplished using a caustic catalyst (basic conditions), such as sodium methoxide ($NaOCH_3$), or the like to both randomize and saponify the saturated wax esters prior to alkoxylation, as will be described below.

In one example embodiment of the present invention, double bonds in the waxes first are hydrogenated (saturated) to create the fully hydrogenated alcohol-free fatty compound. Then the hydrogenated waxes are saponified. The saponification step also randomizes the naturally occurring composition of the fatty acids and fatty alcohols in the esters. Finally the hydrogenated, saponified, and randomized waxes are alkoxylated, thereby producing compositions according to the present invention.

In another embodiment of the present invention, fully hydrogenated waxes and unsaturated waxes are first mixed together. This mixture is then saponified, said saponification resulting in the randomization of the fatty acids and fatty alcohols between, and within, the hydrogenated and unsaturated waxes. The resultant compositions are finally alkoxylated, thereby producing further compositions according to the present invention.

In yet another embodiment of the present invention, different amounts of different trans free and alcohol-free fatty compounds are mixed together and catalytically interesterified (producing a trans-free product) and then followed by alkoxylation.

In still yet another embodiment of the present invention, partially or fully hydrogenated wax esters are mixed with fatty compounds containing unsaturation in the trans isomer form. These mixtures are interesterified and alkoxylated, as described above.

By mixing different amounts of different alcohol-free fatty compounds together and interesterifying the resultant mixture, physical properties, such as melting point, hydrophilic/lipophylic balance, slip, spread, and the like may be varied and set. Alternately, the physical and chemical properties of the interesterified materials can be adjusted by addition of ethylene oxide and/or propylene oxide, in different combinations and ratios. This would adjust the level and amount of randomized, but un-alkoxylated, trans-free, interesterified starting material remaining in the final compositions, thereby further adjusting physical and chemical properties of the compositions according to the present invention.

In one specific embodiment, 150 mole equivalents of the acyl oxide, preferably ethylene oxide is reacted with each mole of fully hydrogenated trans free and alcohol-free transesterified fatty compound, hydrogenated jojoba oil, in the caustic conditions noted above. Resulting majority products, illustrated in FIG. 1, are a combination of polyalkoxylated fatty alcohols (I), polyalkoxylated fatty acids (II), polyalkoxylated diethers (III), polyalkoxylated ethers (IV), and residual unreacted material (V). Other polyalkoxylated minority products (not shown) are possible, even likely, including residual trans-free fully hydrogenated and randomized fatty compounds. The preferred composition according to the present invention has the total mole equivalent amount of acyl oxide added to the hydrogenated trans and alcohol free composition, $\Sigma mol_{q,n}$, $\approx 150$. $\Sigma mol_{q,n}$ may vary from 5 to 400 total mole equivalents and still fall within the scope of the present invention.

The product compositions of the present invention have been found to have beneficial physical properties, such as melting point, hardness, solubility profile, wettability, adhesion, and the like. The preferred composition is moderately soluble in oils and produces a clear solution when mixed with water, at concentrations up to 5%, may create a cloudy mixture at higher concentrations. The HLB number of the preferred composition is 9.6, with a penetrometer reading of 0.68 mm when tested at ambient (20° C.) temperatures. The measured melting point range of the preferred composition is 55–58° C., and the Floratech slip test angle, in a 5% solution, is 17°.

Example formulations using the product of the present invention are described below.

Conditioning Shampoo

Florasolvs Peg-150 Hydrogenated Jojoba esters (the one composition according to the present invention) lends viscosity and foam stabilization to this conditioning shampoo.

| Phase | Trade Name | INCI Name | Supplier | % wt/wt |
|---|---|---|---|---|
| A. | Deionized Water | Water | | Q.S. |
| | Sodium Laureth Sulfate 60% | Sodium Laureth Sulfate | Chemron | 28.00 |
| | Florasolvs PEG 150 Hydrogenated Jojoba | PEG-150 Hydrogenated Jojoba esters | Floratech | 4.00 |
| B. | Floraesters 20 | Jojoba Esters | Floratech | 0.50 |
| | Sodium Lauryl Sulfate 30% | Sodium Lauryl Sulfate | Chemron | 6.00 |
| C. | Lactic Acid | Lactic Acid | Inolex | Q.S. to pH 4 |
| D. | UCARE Polymer JR 30M | Polyquaternium-10 | Amerchol | 0.30 |
| | Lexaine C | Cocamidopropyl Betaine | Inolex | 6.00 |
| | Lexein X-250 | Hydrolyzed Collagen | Inolex | 2.00 |
| | Versene Na2 | Disodium EDTA | Dow | 0.10 |
| E. | Preservative | — | | Q.S. |
| | Fragrance | Fragrance | | Q.S. |
| | Color (optional) | | | Q.S. |
| | | | | 100.00 |

Mixing Procedure
1. Heat water to 70° C. and add Sodium Laureth Sulfate and Florasolves PEG-150 Hydrogenated Jojoba with agitation.
2. Pre-mix Phase B and add to Phase A with propeller agitation.
3. Adjust pH to 4 with Phase C and add UCARE Polymer JR 30M slowly. Add remaining ingredients of Phase D in order with propeller agitation.
4. At 40° C., add ingredients of Phase E with agitation. Cool to room temperature.

Cream Conditioning Shampoo

A cream shampoo with excellent conditioning properties contributed by PEG 150 Hydrogenated Jojoba esters.

| Phase | Trade Name | INCI Name | Supplier | % wt/wt |
|---|---|---|---|---|
| A. | Deionized Water | Water | | Q.S. |
| | Florasolvs PEG-150 Hydrogenated Jojoba | PEG-150 Jojoba Esters | Floratech | 5.00 |
| | Sulfochem SLS | Sodium Lauryl Sulfate | Chemron | 45.00 |
| B. | Lexemul 515 | Glyceryl Stearate | Inolex | 3.00 |
| | Floramac 10 | Ethyl Macadamiate | Floratech | 0.50 |
| | Floraesters IPJ | Jojoba Esters (and) Isopropyl Jojobate (and) Jojoba Alcohol | Floratech | 0.50 |
| | Floraesters 15 | Jojoba Esters | Floratech | 0.50 |
| C. | Chembetaine CGF | Cocamidopropyl Betaine | Chemron | 7.00 |
| | GE Silicone SF 1188 | Dimethicone Copolyol | GE Silicones | 0.50 |
| | Abil Quat 3272 | Quaternium-80 | Goldschmidt | 0.40 |
| D. | Citric Acid (to pH 6.5–6.8) | Citric Acid | Roche | 0.10 |
| | Fragrance | Fragrance | Shaw Mudge Co. | 0.50 |
| | Sodium Chloride | Sodium Chloride | Morton Salt | 0.50 |
| | | | | 100.00 |

Mixing Procedure
1. Heat water to 70° C. Dissolve the Florasolvs PEG-150 Hydrogenated Jojoba with propeller agitation. Add the Sulfochem SLS with propeller agitation.
2. Blend all ingredients of Phase B together with heat till melted. Add Phase B to Phase A with propeller agitation.
3. Lower temperature to 50° C. Add in Phase C ingredients in order with propeller agitation.
4. Add in the Citric Acid powder with propeller agitation.
5. Add in Fragrance and Sodium Chloride with propeller agitation, and allow to cool to room temperature.

Spray Hair Detangler

This formula assists in detangling wet hair and leaving a conditioned, glossy shine contributed by use of PEG-150 Hydrogenated Jojoba esters.

| Phase | Trade Name | INCI Name | Supplier | % wt/wt |
|---|---|---|---|---|
| A. | Deionized Water | Water | — | Q.S. |
| | Propylene Glycol | Propylene Glycol | Dow | 8.00 |
| | Chembetaine CGF | Cocamidopropyl Betaine | Chemron | 3.00 |
| | Florasolvs PEG-150 Hydrogenated Jojoba | PEG-150 Hydrogenated Jojoba Esters | Floratech | 2.00 |
| | GE Silicone Fluid 1188 | Dimethicone Copolyol | GE Silicones | 0.70 |
| | Preservative | — | | Q.S. |
| | | | | 100.00 |

Mixing Procedure
1. Add each of the ingredients in order, allowing time for each to completely dissolve.

Hair Styling Wax

Florasolvs PEG 150 Hydrogenated Jojoba esters provides water-soluble jojoba emolliency, and viscosity adjustment in this hair care product.

| Phase | Trade Name | INCI Name | Supplier | % wt/wt |
|---|---|---|---|---|
| A. | White Petrolatum | Petrolatum | Penreco | 28.50 |
| | Yellow Beeswax SP 6P | Beeswax | Strahl & Pitsch | 6.00 |
| | Bentone Gel VS-5PC | Cyclomethicone (and) Quaternium-18 Hectorite (and) SD Alcohol 40 | Rheox | 5.00 |
| | Florasun 90 | Helianthus Annuus (Sunflower) Seed Oil | Floratech | 5.00 |
| | Floraesters 70 | Jojoba Esters | Floratech | 3.00 |
| | Floraesters 60 | Jojoba Esters | Floratech | 7.00 |
| | Talc Supra H | Talc | Luzenac | 2.00 |
| | Carnauba Wax #1 Yellow SP63 | Copernicia Cerifera (Carnauba) Wax | Strahl & Pitsch | 6.00 |
| B. | Deionized Water | Water | — | Q.S. |
| | Florasolvs PEG-150 Hydrogenated Jojoba | PEG-150 Hydrogenated Jojoba Esters | Floratech | 10.00 |
| | Preservative | — | | Q.S. |
| C. | Fragrance (Bell J-6674-B) | Fragrance | Bell | Q.S. |
| | Covi-Ox T-70 | Tocopherols | Cognis | 1.00 |
| | | TOTAL: | | 100.00 |

Mixing Procedure
1. Combine Phase A ingredients and heat to 90° C. with propeller agitation. Mix for 20 minutes.
2. Add Phase B ingredients and mix at 80° C. with propeller agitation. When Phase B is completely mixed, add slowly to Phase A with fast propeller agitation.
3. Cool to 75° C. and add Phase C components. Pour into containers will still hot and fluid. Allow time to cool to room temperature before use.

Skin Softening Lotion

This lotion spreads easily and absorbs quickly into the skin, leaving it smooth, soft, and supple as a result of the use of PEG 150 Hydrogenated Jojoba esters.

| Phase | Trade Name | INCI Name | Supplier | % wt/wt |
|---|---|---|---|---|
| A. | Floraesters 20 | Jojoba Esters | Floratech | 2.50 |
|  | Floramac Hawaiian Macadamia Nut Oil | Macadamia Integrifolia Seed Oil | Floratech | 2.00 |
|  | Floraesters 30 | Jojoba Esters | Floratech | 5.00 |
|  | Lexemul 561 | Glyceryl Stearate (and) PEG-100 Stearate | Inolex | 3.00 |
|  | Lanette 16 | Cetyl Alcohol | Cognis | 1.00 |
|  | Cosmowax P | Stearyl Alcohol (and) Ceteareth-20 | Croda | 0.50 |
|  | SF 96-200 Silicone Fluid | Dimethicone | GE Silicone | 0.20 |
|  | Preservative | — |  | Q.S. |
| B. | Deionized Water | Water |  | Q.S. |
|  | Florasolvs PEG-150 Hydrogenated Jojoba | PEG-150 Hydrogenated Jojoba Esters | Floratech | 4.00 |
| C. | Propylene Glycol | Propylene Glycol | Dow | 5.00 |
|  | Kelgin HV | Algin | CP Kelco | 0.20 |
|  | Preservative | — |  | Q.S. |
| D. | Fragrance | Fragrance |  | Q.S. |
|  |  |  |  | 100.00 |

Mixing Procedure

1. Heat Phase A to 75° C. with agitation
2. Heat water of Phase B to 75° C. with agitation. Add Florasolvs PEG-150 Hydrogenated Jojoba.
3. Pre-mix Phase C with moderate agitation and add slowly to Phase B with moderate high-speed agitation. Mix for 15 minutes.
4. Add Phase A slowly to Phase BC with propeller agitation.
5. Force cool to 40° C. with agitation. Add fragrance (if desired) and mix with propeller agitation to room temperature.

Deodorant Stick

Florasolvs PEG-150 Hydrogenated Jojoba esters clarify and improve the application properties of this clear deodorant stick.

| Phase | Trade Name | INCI Name | Supplier | % wt/wt |
|---|---|---|---|---|
| A. | Deionized Water | Water |  | Q.S. |
|  | Chloracel | Sodium Aluminum Chlorohydroxy Lactate | Reheis | 17.00 |
| B. | Propylene Glycol, USP | Propylene Glycol | Dow | 33.00 |
|  | Irgasan DP300 | Triclosan | Ciba-Geigy | 0.30 |
|  | Sodium Stearate C-7 | Sodium Stearate | Crompton | 8.00 |
| C. | Florasolvs PEG-150 Hydrogenated Jojoba | PEG-150 Hydrogenated Jojoba Esters | Floratech | 5.00 |
|  | Carsamide CA | Cocamide DEA | Lonza | 2.00 |
|  | Polyglycol E-1450 | PEG-32 | Dow | 4.20 |
| D. | Fragrance | Fragrance |  | Q.S. |
|  | Color (optional) |  |  | Q.S. |
|  |  | TOTAL: |  | 100.00 |

Mixing Procedure

1. Heat water of Phase A to 75° C. Add Chloracel with agitation to dissolve. Cool to 65° C.
2. Combine Phase B and heat to 75° C. with agitation.
3. Add the ingredients of Phase C to Phase B in the given order and mix for 15 minutes. Cool to 65° C.
4. Add Phase BC to A with agitation and mix until uniform.
5. Add color and fragrance.
6. Fill at 62–65° C. Cool in containers at room temperature.

Adhesive Composition

Florasolvs PEG-150 Hydrogenated Jojoba esters may be used essentially by themselves, or in blended with other waxes, oils, thickeners, abrasive materials, pigments, and the like to prepare a "water soluble" adhesive wax. These adhesives are an essentially solvent-free water-soluble ester based adhesive. The adhesive composition imparts soft handle and hydrophilic/lipophilic properties as well as good resiliency and crease resistance. Further, these adhesives show good compatibility with various resins, and therefore are suitable for shape-memory finishing of cellulose fiber and the like.

| Phase | Trade Name | INCI Name | Supplier | % wt/wt |
|---|---|---|---|---|
|  | Florasolvs PEG-150 Hydrogenated Jojoba | PEG-150 Hydrogenated Jojoba Esters | Floratech | 97.00 |
|  | Florasolvs PEG-12 Carnauba |  | Floratech | 3.00 |
|  |  | TOTAL: |  | 100.00 |

Mixing Procedure

1. Combine Florasolvs PEG-150 Hydrogenated Jojoba with Florasolvs PEG-12 Carnauba and heat to 75° C. with agitation.
2. Fill at 62–65° C. Cool in containers at room temperature.

In addition to the essential ingredients in the compositions of the present invention, further material may be present in the composition for functional or aesthetic reason. Antioxidants, including tocotrienols (compounds homologous to tocopherols that differ by the presence of three unsaturated bonds in the phytyl side chain), and oryzanol (a mixture of ferulic acid esters of sterols, e.g., beta-sitosteryl ferulate and methyl ferulate, and triterpene alcohols, e.g., 24-methylenecycloartenyl ferulate; see Bailey's Industrial Oil and Fat Products, 4$^{th}$ Ed., John Wiley, New York, 1979, volume 1, pages 407 to 409) may be present. Fragrances, colorants (e.g., dyes or pigments), topically applied medications, UV absorbers, whitening agents, emulsifying agents, binders, scrubbing particulates, and the like may be present.

Fatty elements used in combination with the present invention can be selected from mineral oils like paraffin or petroleum oils, silicon oils, vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils, animal oils and fats like tallow, lanolin, butter oil, fatty acid esters, fatty alcohol esters, waxes whose melting point is the same as the skin's (animal waxes like beeswax, botanical waxes such as carnauba or candelilla waxes, mineral waxes like micro-crystalline waxes and synthetic waxes like polyethylene or silicone waxes). All acceptable oils used in cosmetology can be used, like the ones that have been mentioned in the CTFA's book, Cosmetic Ingredient Handbook, First edition, 1988, The Cosmetic, Toiletry and Fragrance Association, Inc., Washington (hereinafter, "CTFA").

Cosmetically or dermatologically active substances may be added to the composition of the present invention, meaning active ingredients chosen from anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances may represent from 1 to 20% by weight of the total weight of the composition.

Detergent or foaming agents, for example used in combination with the preferred embodiments, may include disodic cocoamphodiacetate salts; lauroylether sulfosuccinate disodic salts; the vegetable protein acylates; the cocoyl gutamate triethanolamine salts; the lauroyl sarcosinate sodium salts; the glucoside decyl-ethers; and the sodium sulfate lauroyl ethers.

Pasty active compounds like lanolin by-products (acetyl lanolin, lanolin, and lanolin alcohols; cholesterol by-products, like cholesterol esters (12 cholesteryl hydroxy stearate); pantaetythritol hydroxylated esters, linear mono-esters like butyl stearate, arachidyl propionate or stearyl heptanoate, and triglycerides with a fatty chain less that $C_{16}$ can also be used. These substances may be water-soluble, lipid-soluble, or lipid-soluble and water soluble at the same time, or dispersible. They can be chosen from the compounds that are found in the CTFA dictionary at pages 51 to 101.

Surface active agents, cationic, anionic, non-ionic and/or Zwitterionic may be used in combination with the preferred embodiments of the present invention. These surface agents can be chosen, for example, from the hydrophilic surface agents, like glycols, such as hexylene glycol, butylene-1,2 glycol, ethyl-2-hexyl sulfosuccinate; oxyethylene octylphenol (and the salts derived from cocoyl and lauroyl collagen, sorbitan palmitate, and the polyoxyethylene byproducts of sorbitol palmitate esters, salts of fatty chain quaternary ammonium. Suitable anionic surfactants which may be used include water-soluble alkali metal or ammonium salts having alkyl radicals containing from about 8 to about 22 carbon atoms, the term alkyl being used to include the alkyl portion of higher acyl radicals. Examples of suitable synthetic anionic surfactants are sodium or ammonium alkyl sulfates, especially those obtained by sulfating higher ($C_8$–$C_{18}$) alcohols produced, for example, from tallow or coconut oil; alkyl ($C_9$–$C_{20}$) benzene sulfonates, particularly sodium linear secondary alkyl ($C_{10}$–$C_{15}$) benzene sulfonates; alkyl glyceryl ether sulfates, especially those ethers of the higher alcohols derived from tallow or coconut oil and synthetic alcohols derived from petroleum; coconut oil fatty monoglyceride sulfates and sulfonates; salts of sulfuric acid esters of higher ($C_8$–$C_{18}$) fatty alcohol-alkylene oxide, particularly ethylene oxide reaction products; the reaction products of fatty acids such as coconut fatty acids esterified with isoethionic acid and neutralized with sodium hydroxide; sodium and potassium salts of fatty acid amides of methyl taurine; alkane monosulfonates such as those derived from reacting alpha-olefins ($C_8$–$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$–$C_{20}$ alpha-olefins, with $SO_3$ and then neutralizing and hydrolyzing the reaction product. The preferred anionic surfactants are sodium or ammonium ($C_{10}$–$C_{18}$) alkyl sulfates and ($C_{10}$–$C_{18}$) alkyl polyethoxy (1–11 EO, ethylene oxide) sulfates and mixtures thereof having differing water solubilities.

Particularly preferred anionic surfactants comprise a mixture of a $C_{10}$–$C_{18}$ alkyl sodium or ammonium sulfate or sulfonate or a $C_{14}$–$C_{15}$ alpha-olefin sodium or ammonium sulfonate (AOS) and a $C_8$–$C_{12}$ alkyl polyethoxy (2–4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also optional.

The amount of anionic surfactant present in the composition will generally range from about 0 or 1% or 4 to 12% by weight (total ingredients) by weight. The amphoteric or Zwitterionic surfactant, may optionally be present at a level of at least abut 0.1 or at least about 0.25 percent by weight of the total composition, per 1 part by weight of the content of anionic surfactant present in the composition.

Examples of amphoteric surfactants that may be used in combination with the composition of the invention are betaines and compounds that can be broadly described as derivatives of aliphatic secondary and tertiary amines in which the aliphatic radical can be straight chain or branched and wherein one of the aliphatic substituent contains from abut 8 to 18 carbon atoms and one contains an ionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, N-higher alkyl aspartic acids and the products sold under the trade name "Miranol".

Makeup or cosmetic compositions comprising the present invention may also contain as an optional ingredient, a film forming skin tightening agent, particularly a plant derived biological polysaccharide cosmetic ingredient that may be combined with a casein hydrolysate.

The polysaccharides that can be used in the practice of the invention include, for example, lecithin, pectin, karaya gum, locust bean gum, xanthan gum and mixtures thereof. The polysaccharides are preferably used in the present compositions in combination with a casein hydrolysate.

Suitable co-emulsifiers, which may be used in combination with compositions according the present invention, are both known w/o (water in oil) and o/w (oil in water) emulsifiers. Typical examples of fats are glycerides while suitable waxes include inter alia beeswax, paraffin wax or microwaxes. Suitable thickeners are, for example, crosslinked polyacrylic acids and derivatives thereof, polysaccharides, more particularly xanthan gum, guar, agar, alginates and tyloses, carboxymethyl cellulose and hydroxyethyl cellulose, also fatty alcohols, monoglycrides and fatty acids, polyacrylates, polyvinyl alcohol and polyvinyl pyrolidone. In the context of the invention, biogenic agents are, for example, plant extracts, protein hydrolysates and vitamin complexes. Typical film formers are, for example, polyvinyl pyrolidone, vinyl pyrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearl esters are, for example, glycol distearic acid esters, such as ethylene glycol distearate, and also fatty acids and fatty acid monoglycol esters. The dyes used may be selected from many of the substances that are permitted and suitable for cosmetic purposes, as listed for example in the publication "Kosmetische Farbemittel" of the Farbstoffkommission der Deutschen pages 81–106. These dyes are typically used in concentrations of 0.001 to 0.1% by weight, based on the mixture as a whole.

The total percentage content of auxiliaries and additives may be 1 to 50% by weight and may be 5 to 40% by weight, based on the formulation. The formulations may be produced in known manner, i.e. for example by hot, cold, hot/cold or PIT emulsification. These are purely mechanical processes that do not involve a chemical reaction. The cosmetic and/or pharmaceutical formulations may have a water content of 25 to 95% by weight and preferably 50 to 75% by weight.

The following list of cosmetic category codes identifies fields of use for the cosmetic compositions and carriers of the present invention.

TABLE 1

FDA cosmetic category codes

01. Baby products.
    A. Baby shampoos
    B. Lotions, oils, powders and creams
    C. Other baby products
02. Bath preparations
    A. Bath oils, tablets and salts
    B. Bubble Baths
    C. Bath capsules
    D. Other bath preparations
03. Eye makeup preparations
    A. Eyebrow pencil
    B. Eyeliner
    C. Eye shadow
    D. Eye lotion
    E. Eye makeup remover
    F. Mascara
    G. Other eye makeup preparations
04. Fragrance preparations
    A. Cologne and toilet waters
    B. Perfumes
    C. Powders (dusting and talcum, excluding aftershave talc)
    D. Sachets
    E. Other fragrance preparations
05. Hair preparations (non-coloring)
    A. Hair conditioner
    B. Hair spray (aerosol fixatives)
    C. Hair straighteners
    D. Permanent waves
    E. Rinses (non-coloring)
    F. Shampoos (non-coloring)
    G. Tonics, dressings, and other hair grooming aids
    H. Wave sets
    I. Other hair preparations
06. Hair coloring preparations
    A. Hair dyes and colors (all types requiring caution statements and patch tests)
    B. Hair tints
    C. Hair rinses (coloring)
    D. Hair shampoos (coloring)
    E. Hair color sprays (aerosol)
    F. Hair lighteners with color
    G. Hair bleaches
    H. Other hair coloring preparations
07. Makeup preparations (not eye)
    A. Blushers (all types)
    B. Face powders
    C. Foundations
    D. Leg and body paints
    E. Lipstick
    F. Makeup bases
    G. Rouges
    H. Makeup fixatives
    I. Other makeup preparations
08. Manicuring preparations
    A. Basecoats and undercoats
    B. Cuticle softeners
    C. Hair creams and lotions
    D. Nail extenders
    E. Nail polish and enamel TABLE 1-continued FDA cosmetic category codes F. Nail polish and enamel removers
    G. Other manicuring preparations
09. Oral hygiene products
    A. Dentifrices (aerosol, liquid, pastes and powders)
    B. Mouthwashes and breath fresheners (liquids and sprays)
    C. Other oral hygiene products
10. Personal cleanliness
    A. Bar soaps and detergents
    B. Deodorants (underarm)
    C. Douches
    D. Feminine hygiene deodorants
    E. Other personal Cleanliness products
11. Shaving preparations
    A. Aftershave lotion
    B. Beard softeners
    C. Men's talcum
    D. Preshave lotions (all types)
    E. Shaving cream (aerosol, brushless and lather)
    F. Shaving soap (cakes, sticks, etc.)
    G. Other shaving preparations products
12. Skin care preparations (creams, lotions, powder and sprays)
    A. Cleansing (cold creams, cleansing lotions, liquids and pads)
    B. Depilatories
    C. Face and neck (excluding shaving preparations)
    D. Body and hand (excluding shaving preparations)
    E. Foot powders and sprays
    F. Moisturizing
    G. Night
    H. Paste masks (mud packs)
    I. Skin fresheners
    J. Other skin products
13. Suntan preparations
    A. Suntan gels, creams and liquids
    B. Indoor tanning preparations
    C. Other suntan preparations The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A composition comprising an alkoxylated wax ester that is substantially trans carbon-carbon double bond free prior to being alkoxylated, the wax ester is an ethoxylated and/or propoxylated fully hydrogenated jojoba wax ester having 5 to 400 mol equivalents of the total ethylene oxides and propylene oxides.

2. The composition according to claim 1 wherein the alkoxylate is ethylene oxide.

3. The composition according to claim 1 wherein the alkoxylate is propylene oxide.

4. The composition according to claim 1 wherein the alkoxylate is a mixture of ethylene oxide and propylene oxide.

5. The composition according to claim 2 where the alkoxylation is roughly 150 mol equivalents.

6. The composition according to claim 3 where the alkoxylation is roughly 150 mol equivalents.

7. The composition according to claim 4 where the alkoxylation is roughly 150 mol equivalents.

* * * * *